United States Patent [19]
Usher et al.

[11] Patent Number: 5,512,454
[45] Date of Patent: Apr. 30, 1996

[54] ENZYMATIC ACYLATION OF 3-HYDROXYMETHYL CEPHALOSPORINS

[75] Inventors: John J. Usher; Guna Romancik, both of East Syracuse; Michael Politino; David A. Lowe, both of Fayetteville, all of N.Y.

[73] Assignee: Bristol-Myers Squibb Company, New York, N.Y.

[21] Appl. No.: 191,304

[22] Filed: Feb. 3, 1994

[51] Int. Cl.$^6$ .......................... C12P 35/04; C12P 35/06; C12N 9/20
[52] U.S. Cl. ................ 435/47; 435/48; 435/49; 435/50; 435/51; 435/196; 435/197; 435/198; 435/839; 435/911; 435/917
[58] Field of Search ................ 435/47, 48, 49, 435/50, 51, 196, 197, 198, 839, 911, 917

[56] References Cited

U.S. PATENT DOCUMENTS

| | | | |
|---|---|---|---|
| 3,202,656 | 8/1965 | Abraham et al. | 540/230 |
| 3,239,394 | 3/1966 | Walton | 435/51 |
| 3,304,310 | 2/1967 | Hari et al. | 540/230 |
| 3,436,310 | 4/1969 | Arnold et al. | 435/47 |
| 3,522,248 | 7/1970 | Voser | 540/220 |
| 3,532,694 | 10/1970 | Somerfield et al. | 435/47 |
| 3,573,296 | 3/1971 | Johnson et al. | 540/230 |
| 3,641,018 | 2/1972 | Hayes et al. | 540/228 |
| 3,821,208 | 6/1974 | Stables et al. | 540/220 |
| 3,853,863 | 12/1974 | Jackson et al. | 540/220 |
| 3,980,644 | 9/1976 | Lunn | 540/221 |
| 4,414,328 | 11/1983 | Imanaka | 435/47 |
| 4,459,405 | 7/1984 | Hall | 540/228 |
| 4,472,503 | 9/1984 | Matsuo et al. | 435/176 |
| 4,533,632 | 8/1985 | Smith et al. | 435/47 |
| 4,584,371 | 4/1986 | Timko | 540/215 |
| 4,861,716 | 8/1989 | Marcuse et al. | 435/139 |
| 4,892,822 | 1/1990 | Abramowicz et al. | 435/132 |
| 5,220,063 | 6/1993 | Tafesh et al. | 564/135 |
| 5,221,739 | 6/1993 | Wildfeuer | 540/230 |
| 5,229,274 | 7/1993 | Crawford et al. | 435/69.1 |

FOREIGN PATENT DOCUMENTS

| | | |
|---|---|---|
| 0044736A2 | 1/1982 | European Pat. Off. |
| 0109300A2 | 5/1984 | European Pat. Off. |
| 0153874A2 | 9/1985 | European Pat. Off. |
| 0173206A1 | 3/1986 | European Pat. Off. |
| 0320132 | 6/1989 | European Pat. Off. |
| 966222 | 8/1964 | United Kingdom |
| 1121308 | 7/1968 | United Kingdom |
| 1474519 | 5/1977 | United Kingdom |
| 1565053 | 4/1980 | United Kingdom |
| 2060610 | 5/1981 | United Kingdom |
| 2040942 | 2/1983 | United Kingdom |
| WO90/12110 | 10/1990 | WIPO |

OTHER PUBLICATIONS

Ogata, et al, "Preparation of Water-insoluble, Enzymatically Active Derivatives of Subtilisin Type Novo by Cross-linking with Glutaraldehyde," *Biochim. Biophys. Acta*, 159, 403–405 (1968).

Singer, "On The Mechanism of Enzyme Inhibition by Sulfhydryl Reagents," *Journal of Biological Chemistry*, 174, 11–21 (1948).

Malcata, et al, "Use of a Lipase Immobilized in a Membrane Reactor to Hydrolyze the Glycerides of Butteroil," *Biotechnology and Bioengineering*, 38, 853–868 (1991).

Newton, et al, "Cephalosporin C, a New Antibiotic Containing Sulphur and D-α-Aminoadipic Acid," *Nature*, 175, 548 (1955).

Andrisano, et al, "Extraction of Cephalsporic C from Fermentation Broths via Lipophilic Intermediates and the Production of 7–Aminocephalosporanic Acid (7–ACA)," *J. Appl. Chem. Biotechnol.*, 26, 459–468 (1976).

Moris, et al, "A Useful and Versatile Procedure for the Acylation of Nucleosides through an Enzymatic Reaction," *J. Org. Chem.*, 58, 653–660 (1993).

Gotor, et al, "Enantioselective Acylation of Amino Alcohols by Porcine Pancreatic Lipase," *J. Chem. Soc., Chem. Commun.*, 957–958 (1988).

Nageo, et al, "Synthesis of O–Acyl–L–Homoserine by Lipase," *JAOCS*, 66(5), 710–713 (1989).

Akita, et al, "Enantioselective Acetylation of an α–Hydroxy Ester by Using Ether–Linked Lipid–Lipase Aggregates in Organic Solvents," *Chem. Pharm. Bull.*, 41(1), 16–20 (1993).

Adelhorst, et al, "Enzyme Catalysed Preparation of 6–O–Acylglucopyranosides," *Synthesis*, 112–115 (1990).

Nicolosi, et al, "Lipase–catalyzed Regioselective Protection of Hydroxy Groups in Aromatic Dihydroxyaldehydes and Ketones," *Tetrahedron*, 49, 3143–3148 (1993).

Panza, et al, "Selective Lipase–catalyzed Acylation of 4,5–O–Benzylidene–D–Glucopyranosides to Synthetically Useful Esters," *Tetrahedron: Asymmetry*, 4(5), 931–932 (1993).

Kato, et al, "Enzymatic synthesis of Amoxicillin by the Cell–Bound α–Amino Acid Ester Hydrolase of *Xanthomonas citri*," *Agric. Biol. Chem.*, 44(4), 821–825 (1980).

Jeffrey, et al, "Deacetylcephalosporin C," *Biochemical Journal*, 81, 591–596 (1961).

*Primary Examiner*—David M. Naff
*Assistant Examiner*—L. Blaine Lankford
*Attorney, Agent, or Firm*—Thomas R. Savitsky

[57] ABSTRACT

O-acylated cephalosporins are produced by reacting 3-hydroxymethylcephalosporins with an acyl donor containing at least three carbon atoms and an enzyme which is a *Rodosporidium toruloides* esterase, a wheat germ lipase, an *Aspergillus niger* lipase, an orange peel acetylesterase or a *Bacillus subtilis* esterase. A preferred enzyme is the esterase from *Rodosporidium toruloides* ATCC 10657. The enzyme can be used while in whole cells or in soluble or inmobilized form.

20 Claims, 3 Drawing Sheets

ENZYMATIC ACYLATION OF 3-HYDROXYMETHYL CEPHALOSPORINS

FIELD OF THE INVENTION

The invention concerns a process for preparing beta lactam antibiotic intermediates involving enzymatic acrylation of 3-hydroxymethyl cephalosporins.

BACKGROUND OF THE INVENTION

3-Acetoxymethyl-β-aminoceph-3-em-4-carboxylic acid (7-ACA) is of primary importance as a starting material for the preparation of semi-synthetic commercial cephalosportns antibiotics. This intermediate is produced commercially from cephalosporin C, a fermentation product of *Cephalosporin acremonium* (see Newton and Abraham, *Nature* 175,548, 1955), by hydrolysis of the D-α-aminoadipyl side chain, either chemically or enzymatically. 3-Hydroxymethyl-7β-aminoceph-3-em-4-carboxylic acid (des-7-ACA) is usually produced as an unwanted side product in the preparation of 7-ACA caused by either the chemical or enzymic (esterase) hydrolysis of the 3-acetyl group. Des-7-ACA can be produced by the action of various esterases on 7-ACA. In addition, it can be produced from desacetyl-cephalosporin C by enzymic hydrolysis in a manner analogous to the conversion of cephalosporin C to 7-ACA (World Patent No. WO 90/12110). As a result of the highly reactive nature of the C-7 amino group, chemical synthesis of 7-ACA from the deacetylated precursor results in a mixture of products. The use of typical chemical acylating reagents such as acetyl chloride or acetic anhydride produces inter alia 7-ACA, N-acetyl 7-ACA and N-acetyl desacetyl 7-ACA. In addition, 3-hydroxymethyl-7β-aminoceph-3-em4-carboxylic acids are susceptible to lactonization under these conditions. Prior art methods of O-acylation involve blocking the reactive G-7 amino group, then performing O-acylation in a non-polar, organic solvent in the presence of a 4-(tertiary amino) pyridine catalyst wish an acid-acceptor base and then deblocklng the C-7 amino group (European Patent No. 153,874A). Further methods comprise of esterifying the 4-position carboxyl group of the C-7 acylated compound to prevent lactonization during the reaction, and deesterifying the carboxyl group and deprotecting the C-7 amino group to produce the 3-alkanoyloxymethyl-7β-aminoceph-3-em-4-carboxylic acid (U.S. Pat. No. 3,532, 694), or performing the O-acylation in an aqueous medium in the presence of a 4-(tertiary amino)pyridine catalyst with an acid-acceptor base and then deblocklng the C-7 amino group (European Patent No. 0230972). In addition, a chemical process for acetylating the 3-hydroxymethyl cephalosporins in an aqueous solvent has been described (U.S. Pat. No. 5,221,739).

Certain esterases and lipases are known to catalyze not only hydrolytic reactions but, with certain substrates, can also be used in the synthetic direction to esterify and transesterify. The use of esterases to produce desacetyl cephalosporin derivatives was first demonstrated by Jeffrey, et al. in *Biochem. J.*, 81, 591–596 (1961) using citrus acetyl esterase (U.S. Pat. No. 3,202,656, European Patent No. 0 109 300). Subsequently, many other esterases and lipases with the ability to deacetylate cephalosporin compounds have been discovered from Aureobasidium (European Patent No. 0 044 736), Schizomycetes (U.S. Pat. No. 3,239, 394), Rhizobium (U.S. Pat. No. 3,436,310), *Bacillus subtilis* (U.S. Pat. No. 3,304,310, European Patent No. 0 173 206), *Rhodosporidium toruloides* (British Pat. No. 2,060,610), *Rhodotorula rubra* (British Patent No. 1,474,519) and wheat germ. More recently, Wang, Y-F., et al. *J. Org. Chem.*, 53, 3129–3130 (1988) reported the use of isopropenyl acetate as an irreversible acyl transfer reagent in the lipase-catalyzed acetylation of sugars.

We have unexpectedly discovered that use of certain enzymes, as hereinafter described, with certain acyl donors, as hereinafter described, function in the synthetic direction to produce cephalosporins acylated at the C-3' position.

SUMMARY OF THE INVENTION

The present invention is advantageous for producing O-acylated cephalosporins in that blocking the amino group at position C-7 is not required and lactonization is eliminated. The specificity inherent in enzymatic reactions allows the selective acylation of the C-3' position without producing the side products typical of the chemical reaction. More specifically, the present invention is directed to an acylation process for the preparation of a cephalosporin compound of the formula (I)

wherein R' is hydrogen or an acyl group of the formula

R—C— wherein R is the residue of a carboxylic acid, X is hydrogen or halo, and G is oxygen, sulphur, sulfoxide, sulphone, or methylene; which comprises reacting a compound of the formula (II)

with an acyl donor in an aqueous medium in the presence of a lipase or esterase enzyme obtained from *Rhodosporidium toruloides*, wheat germ, orange peel, *Bacillus subtilis*, or *Aspergillus niger.*

DETAILED DESCRIPTION OF THE INVENTION

The acyl donors for use in the present invention contain at least three carbon atoms and are those which drive the reaction at the C-3' position in the synthetic direction. Such acyl donors are acetyl donors or monohalo acetyl donors.

Acyl donors can be "reversible" or "irreversible" donors. Reversible donors include ethyl acetate and triacetin. These esters and the alcohol (compound of Formula II) are brought into equilibrium with the product (compound of Formula I) and the alcohol from the ester. For example, with ethyl acetate, the reaction is as follows:

Ester      Alcohol (II)

Ester (I)      Alcohol

This reaction will work in the reverse direction to give, from ester I and ethanol, a mixture of ethyl acetate and the alcohol II. With the irreversible donors, such as isopropenyl acetate, the alcohol resulting from the transesterification

ENOL      ACETONE is unstable and tautomerizes to give acetone. This acetone is unable to participate in the back reaction as with the "reversible" type donor. There is, therefore, a driving force in the direction of the formation of the acetylated product (I)

and yields are correspondingly better.

Examples of acyl donors of use in the present invention have the formula (III)

wherein R" is $C_1-C_{10}$ alkyl, $C_2-C_{10}$ alkenyl, $C_3-C_{10}$ cycloalkyl, $C_3-C_{10}$ cycloalkenyl, $C_2-C_{10}$ alkynyl, $C_6-C_{30}$ aryl, $C_1-C_{10}$ substituted alkyl, $C_2-C_{10}$ substituted alkenyl, $C_3-C_{10}$ substituted cycloalkyl, $C_3-C_{10}$ substituted cycloalkenyl, $C_6-C_{30}$ substituted aryl, a group of the formula wherein n is an integer of 2 or greater (preferably 2 to 3,000, more preferably 2 to 100) and R''' is H or acetyl, or group of the formula wherein n and R''' are as defined above; and X is hydrogen or halo.

Preferred acyl donors are wherein R" is $C_2-C_6$ alkenyl, $C_1-C_6$ alkyl substituted with 1–3 acetoxy groups, $C_6-C10$ aryl, or a group of the formula wherein n is an integer of 2 to 100.

Specific examples of acyl donors include isopropenyl acetate, triacetin, vinyl acetate, ethyl acetate, diacetin, ethylene glycol diacetate, cis-1,4-diacetoxy butane, 1,4-diacetoxy butane, phenyl acetate, 1,2,4-triacetoxy benzene, 1,3-butanedial diacetate, 1,2-propanediol diacetate, n-butyl acetate, triethylene glycol diacetate, isopropyl acetate, and isobutyl acetate, and the like.

More preferred acyl donors are isopropenyl acetate, triacetin, vinyl acetate, diacetin, ethylene glycol diacetate, cis-1,4-diacetoxy butane, 1,4-diacetoxy butane, phenyl acetate, 1,3-butanediol diacetate, 1,2-propanediol diacetate, or triethylene glycol diacetate.

R' is the "residue of a carboxylic acid" which includes those $C_7$-position side chains known in the cephalosporin art and those $C_6$-position side chains known in the penicillin art. Normally, these side chains are those in which R is the residue of a $C_1-C_{20}$ carboxylic acid, and are exemplified when R is hydrogen, $C_1-C_6$ alkyl, $C_1-C_6$ alkyl substituted by cyano, carboxy, halogen, amino, $C_1-C_4$ alkoxy, $C_1-C_4$ alkylthio, trifluoromethyl or trifluoromethylthio; naphthyl, phenyl or substituted phenyl group of the formula wherein a and a' independently are hydrogen, halogen, cyano, nitro, hydroxy, $C_1-C_4$ alkoxy, $C_1-C_4$ alkanoyloxy, $C_1-C_4$ alkyl, $C_1-C_4$ alkylthio, amino, $C_1-C_4$ alkanoylamino, $C_1-C_4$ alkylsulfonylamino, carboxy, carbamoyl, hydroxymethyl, aminomethyl, or carboxymethyl; a group of the formula wherein a and a' have the same meanings as defined above, Z is O or S, and m is 0 or 1; an arylmethyl group of the formula wherein $R_3$ is naphthyl, thienyl, furyl, benzothienyl, benzoaminothiazolyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and said arylmethyl groups substituted by amino, hydroxy, cyano, nitro, halogen, $C_1-C_4$ alkyl, $C_1-C_4$alkoxy, phenyl or substituted phenyl or $C_1$–$C_4$alkylsulfonylamino; a substituted methyl group of the formula wherein $R_4$ is cyclohex-1,4-dienyl, a phenyl or substituted phenyl of the formula wherein a and a' are as defined above, or $R_4$ is $R_3$ as defined above, and Q is hydroxy, $C_{1-4}$ alkanoyloxy, carboxy, sulfo, amino, sulfamino, or a substituted amino group of the formula wherein $R^x$ is hydrogen or $C_1$–$C_4$ alkyl, $R^y$ is $C_1$–$C_4$ alkyl, furyl, thienyl, phenyl, halophenyl, nitrophenyl, styryl, halostyryl, nitrostyryl or a group of the formula wherein $R^x$ has the same meanings as defined above and R2 is hydrogen, $C_1$–$C_4$ alkylsulfonyl, $C_1$–$C_4$ alkyl, or $C_1$–$C_4$ alkanoyl; or Q is a substituted amino group of the formula wherein $R^2$ has the same meaning as defined above, and q is 2 or 3; or Q is a substituted amino group of the formula or Q is a benzamido group of the formula wherein x is 1 to 3; or Q is a pyridone or pyridonylcarbonylamino group of the formula wherein $R^x$ is as defined above; or Q is a pyridyl-carbonylamino group of the formula said group optionally substituted by $C_1$–$C_4$ alkyl, amino, carboxy, hydroxy or halogen; or Q is an imidazolyl or pyrazolyl group of the formula or and said imidazolyl or pyrazolyl optionally substituted by $C_1$–$C_4$ alkyl, carboxy, amino or halogen; or Q is a benzpyridazin-4-one group or tautomer thereof represented by the formula or wherein $R^x$ is as defined above, and t is 1 to 3; or Q is a benzpyranone group of the formula or R is a group of the formula wherein $R_5$ is $R_3$ or $R_4$ as defined above, $R_9$ is hydrogen or halogen, and $R_6$ is hydrogen, $C_1$–$C_4$ alkyl, $C_1$–$C_4$ alkyl substituted by halogen, a carboxy-substituted alkyl or cycloalkyl group represented by the formula wherein b and b' independently are hydrogen or $C_1$–$C_3$ alkyl; n is 0, 1, 2, or 3; or b and b' when taken together with the carbon to which they are bonded form a 3- to 6-membered carbocyclic ring; and $R_7$ is hydroxy, $C_1$–$C_4$ amino, $C_1$–$C_4$alkylamino, or di($C_1$–$_4$ alkyl)amino; or $R_6$ is $C_1$–$C_4$ alkyl substituted by phenyl or phenyl substituted by one or two of the same or different groups selected from among $C_1$–$C_4$alkyl, hydroxy, halogen, carboxy or protected carboxy; or $R_6$ is $C_1$–$C_4$ alkenyl; or $R_6$ is a cyclic lactam group of the formula wherein:

v is 2–4 and $R_8$ is hydrogen or $C_1$–$C_3$ alkyl; or $R_6$ is an aryl methyl group of the formula

$R_3$ has the same meaning as defined hereinabove; or

R is a group of the formula

—(CH$_2$)$_t$COOH wherein t is as defined previously; or

R is a group of the formula wherein t is as defined above; or

R is a group of the formula wherein t is as defined above, $R_{12}$ is hydrogen and $R_{11}$ is phenyl, substituted phenyl, or a group of the formula wherein $R_{13}$ may be phenyl, substituted phenyl, $C_1$–$C_6$ alkyl, $C_1$–$C_6$ substituted alkyl, aminophenyl, phenylsulfonyl, (substituted phenyl)sulfonyl, $C_1$–$C_4$ alkoxy, or oxo($C_1$–$C_6$ alkyl).

In the above definition of the compounds represented by the various formulae (i.e., Formulae I, II and III) "alkyl" refers to the straight and branched chain alkyl groups such as methyl, ethyl, n-propyl, isopropyl, n-butyl, s-butyl, t-butyl, n-pentyl, n-hexyl, 3-methylpentyl, and like alkyl groups; "substituted alkyl" includes those alkyls substituted with cyano, carboxy, halogen, amino, $C_1$–$C_4$alkoxy, $C_1$–$C_4$ alkylthio, trifluoromethyl, and trifluoromethylthio; "alkyl substituted . . . by cyano" refers to cyanomethyl, cyanoethyl, 4-cyanobutyl, and the like; "alkyl substituted by . . . carboxy" refers to such groups as carboxymethyl, 2-carboxyethyl, 2-carboxypropyl, 4-carboxybutyl, 5-carboxypentyl, and the like; "alkyl substituted by . . . halogen" refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; "alkyl substituted by . . . amino" refers to such groups as 2-aminoethyl, aminomethyl, 3-aminopropyl and 4-aminobutyl; "alkyl substituted by . . . $C_1$–$C_4$alkoxy" refers to methoxymethyl, 2-methoxyethyl, 2-ethoxyethyl, ethoxymethyl, 3-propoxypropyl, 3-ethoxybutyl, 4-t-butoxybutyl, 3-methoxypentyl, 6-methoxyhexyl, and like groups; "alkyl substituted by . . . $C_1$–$C_4$ alkylthio" refers to such groups as for example methylthiomethyl, 2-methylthioethyl, 2-ethylthiopropyl, 4-methylthiobutyl, 5-ethylthiohexyl, 3-t-butylthiopropyl, and like groups; "alkyl substituted by . . . trifluoromethyl" is exemplified by 2,2,2-trifluoroethyl, 3,3,3-trifluoropropyl, 4,4,4-trifluorobutyl, 6,6,6-trifluorohexyl, and the like; and "alkyl substituted by . . . trifluoromethylthio" refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

The term "alkenyl" denotes groups possessing at least one double carbon-carbon bond. A few examples of such groups are vinyl, 1-propene-2-yl, 1-butene-4-yl, 1-pentyne-1-yl, 1-butyne-1-yl, and like groups.

The term "substituted alkenyl" denotes groups possessing at least one double carbon-carbon bond, and substituted with one or more of halo, carboxy, amino, $C_1$–$C_4$alkoxy, $C_1$–$C_4$ alkylthio, trifluoromethyl, trifluoromethyl-thio, cyano, and the like.

The term "alkynyl" denotes groups possessing at least one triple carbon-carbon bond. A few examples of such groups are ethynyl, propynyl, and like groups.

The term "cycloalkyl" denotes cyclic alkyl groups having at least 3 carbon atoms. A few examples of such groups are cyclopropyl, cyclohexyl, and like groups.

The term "substituted cycloalkyl" denotes cyclic alkyl groups substituted with one or more of halo, carboxy, amino, $C_1$–$C_4$ alkoxy, $C_1$–$C_4$ alkylthio, trifluoromethyl, trifluoromethylthio, cyano, and the like.

The term "aryl" denotes cyclic groups of an aromatic nature. Examples of such groups include phenyl, naphthyl, and anthyl.

The term "substituted aryl" denotes aryl groups substituted with one or more of halo, carboxy, amino, $C_1$–$C_4$alkoxy, $C_1$–$C_4$ alkylthio, trifluoromethyl, trifluoromethylthio, cyano, and the like.

The term "$C_1$–$C_4$ alkylthio" refers to those groups possessing one to four carbon atoms and substituted with at least one sulfur atom.

The terms "halo" and "halogen" refer to the fluoro, chloro, bromo or iodo groups.

In the Formula I, substituted phenyl groups wherein the substituent(s) are represented by a and a' are exemplified by such groups as halophenyl such as 4–chlorophenyl, 3–bromo-phenyl, 2–fluorophenyl, 2–iodophenyl, 2,4–dichlorophenyl, and 3,5-di-chlorophenyl; hydroxyphenyl such as 2-hydroxy-phenyl, 3-hydroxyphenyl, 4-hydroxyphenyl, 2,4-dihydroxy-phenyl, dihydroxy-phenyl, and 3,4-dihydroxyphenyl; alkoxyphenyl, such as 2,6-dimethoxyphenyl, 4-methoxyphenyl, 3-ethoxyphenyl, 3,4-dimethoxyphenyl, 4-t-butoxyphenyl, 4-methoxy-3-ethoxyphenyl, and 4-n-propoxyphenyl; alkanoyloxyphenyl such as 2-acetoxyphenyl, 4-propionoxyphenyl, 4-formyloxyphenyl, 4-acetoxyphenyl, 3-butyryloxyphenyl, and 3-acetoxyphenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such as 3-methylsulfonylamino-phenyl, 4-methylsulfonylaminophenyl, 3,5-di(methylsulfonylamino)phenyl, 4-n-butylsulfonylaminophenyl, and 3-ethylsulfonylaminophenyl; carboxyphenyl such as 2-, 3-, or 4carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-di-carboxymethyl)phenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxymethyl-4-hydroxyphenyl.

Examples of RCO—groups of the Formula I wherein R is a group represented by the formula with m=0 are: phenylacetyl, 4-hydroxyphenylacetyl, 4-chlorophenylacetyl, 3,4-dichlorophenylacetyl, 4-methoxyphenylacetyl, 3-ethoxyphenylacetyl, 2-aminomethylphenylacetyl, 3-carboxyphenylacetyl, 4-acetoxyphenylacetyl, 3-aminophenylacetyl, and 4-acetylaminophenylacetyl; and with m=1 and Z=0, phenoxyacetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethylphenoxyacetyl; and with m=1 and Z-S, phenylthioacetyl, 4 -chlorophenylthioacetyl, 3,4-dichlorophenylthioacetyl, 2-fluorophenylthioacetyl, 3-hydroxyphenylthioacetyl, and 4-ethoxyphenylthioacetyl.

Examples of $R_3$—$CO_2CO$— groups of the Formula I wherein $R_3$ is a heteroaryl group are: 2-thienylacetyl, 3-thienylacetyl, 2-furylacetyl, 2-benzothienylacetyl, 2-benzofurylacetyl, indol-2-ylacetyl, 1H-tetrazol-l-ylacetyl, oxazol-2ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-ylacetyl, 5-ethyl-1,3,4-thiadiazol-2-ylacetyl, and like heteroaryl groups substituted by amino, $C_1$–$C_4$alkylsulfonylamino, hydroxy, halo, $C_1$–$C_4$ alkyl or $C_1$–$C_4$alkoxy groups.

Examples of RCO— groups of the Formula I compounds wherein R is a substituted methyl group represented by the formula $R_4$-CH(Q)- and Q is amino, carboxy, hydroxy, or sulfo, are 2-carboxy-2-phenylacetyl, 2-amino-2-(2naphthalenyl)acetyl, 2-carboxy-2-(4-hydroxyphenyl)acetyl, 2-amino-2-phenylacetyl, amino-2-phenylacetyl, 2-amino-2-(4-hydroxyphenyl)acetyl, 2-amino-2-amino-2-(3-chloro-4-hydroxyphenyl)acetyl, 2-amino-2-(cyclohex-1,4-dienyl)acetyl, 2-amino-2-(3-methylsulfonamidophenyl)acetyl, 2-amino-2-(3-methylsulfonamidophenyl)acetyl, 2-amino-2-(3-ethylsulfonaminophenyl)acetyl, 2-hydroxy-2-phenylacetyl, 2-formyloxy-2-phenylacetyl, 2-sulfo2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2yl)acetyl, 2-amino-2-(2-aminothiazol-4-yl)acetyl, 2-carboxy-2-(2-thienyl)acetyl, 2-(2-thienyl)acetyl, 2-carboxy-2-(benzothien-2-yl)acetyl, and 2-hydroxy-2-(benzofur-2-yl)acetyl; and when Q is a substituted amino group represented by the formula examples of such acyl groups are 2-(N-methyl-N-benzoylcarbaoylamino-2-phenylacetyl, 2-(N-methyl-N-cinnamoylcarbamoylamino)-2-(2-furyl)acetyl, 2-(N,N-dimethylcarbamoylureido)-2-(4-chlorophenyl)acetyl, 2-[N-methyl-N-(2-chlorocinnamoyl)carbamoylamino]-2-(2-thienyl)acetyl, and 2-(N-ethyl-N-acetylcarbamoylamino)-2-(4-hydroxyphenyl) acetyl; and when Q is a substituted amino group represented by the formula examples are 2-[(3-methylimidazolidin-2-one-1-yl)carbonylamino]-2-phenylacetyl, 2-[(3-acetylimidazolidin-2-one-1yl)carbonylamino]-2-phenylacetyl, 2-[(3-methylsulfonylimidazolidin-2-one -1yl)-2-thienyl)acetyl, and 2-[(3-acetylhexahydropyrimidin-2-one-1-yl)carbonylamino]-2phenylacetyl; and when Q is a hydroxy-substituted benzamido group represented by the formula examples of such acyl groups are 2-(2,4-dihydroxybenzamido)-2-phenylacetyl, 2-(4-hydroxybenzamido)-2-(4-hydroxyphenyl)-acetyl, 2-(3,4-dihydroxybenzamido)-2-(2-aminothiazol-4-yl)-acetyl, 2-(3,5-dihydroxybenzamido)-2-(3-thienyl) acetyl, and 2 -(2 -hydroxybenzamido)-2 -(2-benzofuryl) acetyl.

When Q is an hydroxy-substituted pyridinecarbonylamino group, examples include e.g., 2-hydroxypyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-ylcarbonylamino, and 4-ami- nopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-ylcarbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae and Examples of RCO acyl groups of the compounds represented by Formula I when R is keto group or an oximino-substituted group represented by the formulae are the keto groups 2-oxo-2-phenylacetyl, 2-oxo-2-(2-thienyl)acetyl, 2-oxo-2-(2-aminothiazol-4-yl)acetyl; and oximino-substituted groups 2-phenyl-2,methoxyaminoacetyl, 2(2-thienyl)-2-ethoxyiminoacetyl, 2-(2-furyl)-2-methoxyiminoacetyl, 2-(2-benzothienyl)-2-carboxymethoxyiminoacetyl, 2-(2-thienyl)-2-(2-carboxyethoxy)iminoacetyl, 2-(2-amino 1,2,4-thiadiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-carbamoyl-prop-2-yl)oxyiminoacetyl, 2-(5-amino-1,3,4-thiadiazol-2-yl)-2-methoxyiminoacetyl.

When $R_6$ of Formula (I) is $C_1-C_4$ alkyl substituted by phenyl or substituted phenyl, such groups are exemplified by benzyl, 4-hydroxybenzyl, 4-chlorobenzyl, 3-carboxybenzyl, 3- cloro-4-hydroxybenzyl, 2-phenylethyl, 1-phenylethyl, 3phenylpropyl, 4-hydroxy-2-phenylpropyl, 3-phenylbutyl and like phenyl-alkyl groups.

When $R_6$ represents $C_1-C_4$ alkyl substituted by amino or protected amino, examples include 2-aminoethyl, 3-aminopropyl, 4-aminobutyl, 2-aminopropyl and such groups wherein the amino group is protected by an amino-protecting group.

When $R_6$ is a $C_2-C_4$ alkenyl group, examples include allyl, butene-2, butene-3, butene-1, and like groups.

Examples of the compounds represented by Formula (I) when R is a group of the formula may be found in Hamashima, U.S. Pat. No. 4,634,617 incorporated herein by reference. Exemplary substituents are, for $R_9$, hydrogen, for $R_5$phenyl, furyl, thienyl, oxazolyl, isoxazolyl, optimally protected aminoisoxazolyl, thiazolyl, optionally protected aminothiazolyl, thiadiazolyl, and aminothiazolyl, and for $R_6$, $C_1-C_3$ alkenyl and $-CH_2COOH$.

When R is a group of the formula $$-(CH_2)_1CH(R_{12}NR_{11})COOH$$

when $R_{12}$, is hydrogen, include:

or $R_{11}$ and $R_{12}$ may together form the group

Further examples of such $R_{11}$ and $R_{12}$ groups may be found in the following U.S. Pat. Nos.: 3,853,863; 3,522,248; 3,573,296; 3,641,018, 3,980,644; and 3,821,208; in the following Japanese Patent Nos.: 108,085 (1976); 2,892 (1978); 53,689 (1978); 029,493 (1976); 13,389 (1973);

149,694 (1975); 82,791 (1977); in the following German Patent Nos.: 2,157,693; 2,721,731; 2,507,117; 2,208,631; 2,458,554; 2,418,088; 2,523,280; and 2,841,363; in the Belgium Patent No. 796,540 (1973); in the British Patent Nos. 1,565,053 and 2,040,942; and in the following article: Andrisano, R., et al., *J. Appl. Chem. Biotechnol.*, (1976), 26, 459–468; all of the above being herein incorporated by reference.

The most preferred R' in the compounds of Formula I and Formula II are hydrogen, acetyl, glutaryl, α-aminodipyl, and phenylacetyl; G is most preferably sulphur; and X is preferably hydrogen.

The enzyme used to perform the acylation process of the invention is a lipase or esterase obtained from *Rhodosporidium toruloides*, wheat germ, orange peel, *Bacillus subtilis* or *Aspergillus niger*.

The enzymes may be used in any form. For example, they may be in crude form, partially purified, or purified to crystallization. If the enzyme is obtained from a microorganism, the process may be performed with whole cells where the enzyme is formed in situ, or soluble enzymes may be obtained after a suitable treatment of cells.

In general, the enzyme will be in a form that can be readily distributed in the reaction medium to be in contact with the acyl donor and starting compound of Formula II. Thus, where the enzyme comes from a microorganism, a sample of the whole culture of the cells may be employed, preferably after treatment to render the cells non-viable, and, if desired, after rupture of the cells, for example, by conventional methods such as ultrasonic treatment, treatment with lytic enzymes or treatment with detergents. Other preparations of cells, which permit their storage with retention of enzyme activity may also be used, for example, acetone dried powders or acetone treated cells. A preferred treatment is with chelating agents such as ethylenediaminetetra acetic acid (EDTA).

The microbial enzyme may also be employed in cell-free form. Thus, a filtrate or supernatant obtained from the culture may be employed. If desired, the cells may be ruptured, for example, as described above, before filtration or centrifugation. Alternatively, the cell free enzyme may be further purified by conventional means. The techniques which may be used include precipitation of the enzyme, e.g. with salts or with organic solvents, such as acetone, chromatography, e.g. on ion-exchange resins or on supports with a special affinity for the enzyme, and desalting, e.g. gel filtration or dialysis. The cell-free enzyme may be used as a solution, as a precipitate or as a suitably immobilized preparation.

Where the enzyme comes from wheat germ or orange peel it is desirable to use an enzyme-containing extract of the plant material. Such an extract may be prepared by conventional methods, which will in general involve initial release of the enzyme from the plant material by physical techniques, such as grinding or pressing as described in British Patent Specification No. 966,222, or by chemical techniques, for example by treatment of the plant material with a hydrocarbon solvent such as petroleum ether, as described in British Patent Specification No. 1,121,308. The resulting preparation, either with or without removal of cell debris may be added directly to the reaction mixture. Alternatively, if desired, the preparation may be treated further, for example, using the techniques described above for microbial enzymes, to obtain a cell-free enzyme which may be used as described for the microbial enzyme.

A preferred preparative procedure is to insolubilize the enzyme by glutaraldehyde/polyethylenimine (PEI) treatment of soluble enzyme. Such insolubilization techniques are well known in the art as disclosed by, for example, Ogata, Ottesen & Svendsen, *Biochim. Biophys. Acta*, 159, 1968, 403–405.

The wheat germ lipase useful in the present invention is well known in the art. Such a lipase is described by, for example, Singer, *J. Biol. Chem.*, 174, 1948, 11, and can be further purified as described in this publication. A commercial source of suitable wheat germ lipase is Wheat Germ Lipase Type I (Cat. No. L 3001), available from Sigma Chemical Company, St. Louis, Mo.

Suitable orange peel esterases useful herein are well known in the art. Such esterases are described in, for example, British Patent Application 966,222, U.S. Pat. No. 3,202,656, and European Patent No. 0 109 300, and can be prepared by methods described in these patents. A commercial source of suitable orange peel esterase includes acetylesterase (Cat. No. A 4530) available from Sigma Chemical Company, St. Louis, Mo.

Suitable lipases obtained from *Aspergillus niger* useful herein are well known in the art. Such a lipase is described by Malcata, Hill and Amundson, *Biotechnol. Bioeng.*, 38, 1991, 853–868. Such lipases can be prepared by fermentation of a lipase-producing strain of *Aspergillus niger* using media and growth conditions well known in the art. A commercial source of the lipase obtained from *Aspergillus niger* is available from Biocatalysts, Ltd., Main Ave., Treforest Industrial Estate, Pontypridd, Mid Glamorgan, CS37 5UT, United Kingdom.

A suitable esterase obtained from *Bacillus subtilis* useful herein is well known in the art. Such an esterase is described in, for example, U.S. Pat. No. 3,304,310 and European Patent No. 0173206. Such esterases can be prepared by fermentation of an esterase-producing strain of *Bacillus subtilis* using media and growth conditions well known in the art. Preferred strains of *Bacillus subtilis* include ATCC 6633 and ATCC 9466.

A suitable esterase obtained from *Rhodosporidium toruloides* useful herein is well known in the art. Such an esterase is described in, for example, British Patent 2060610. Such an esterase can be prepared by fermentation of an esterase-producing strain of *Rhodosporidium toruloides* using media and growth conditions well known in the art. Preferred strains of *Rhodosporidium toruloides* include ATCC 10657.

Routine experimentation will determine the amount of enzyme required in the process which can vary depending upon the source, purity, reaction conditions, and the like.

The process of the invention is performed in an aqueous medium. For example, the process can be performed in water or a fermentation broth suitable for culturing a lipase or esterase producing organism. The ability to carry out the process of the invention in water enables the acylation to be accomplished at an early stage in purification from the broth. Further, as the process is carried out in an aqueous medium, it does not require the transfer of the broth mixture to a solvent in order to accomplish the acylation. Growth of the microorganisms may be achieved by one of ordinary skill in the art by the use of an appropriate medium. Aerobic conditions with shaking or stirring are preferably employed. Appropriate media for growing microorganisms include those which provide nutrients necessary for the growth of the microbial cells. A typical medium for growth includes necessary carbon sources, nitrogen sources, and trace elements.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; and alcohols such as ethanol, propanol and the like.

Nitrogen sources may include N-Z amine A, corn steep liquor, soy bean meal, beef extracts, yeast extracts, molasses, baker's yeast, tryptone, nutrisoy, peptone, yeastamin, sodium nitrate, ammonium sulfate and the like.

Trace elements may include phosphates and magnesium, manganese, calcium, cobalt, nickel, iron, sodium and potassium salts.

The medium employed may include more than one carbon or nitrogen source or other nutrient.

Suitable techniques for culturing *Aspergillus niger* are described in ATCC Catalogue of Filamentous Fungi, American Type Culture Collection, Rockville, MD; suitable techniques for culturing *Bacillus subtilis* are described in U.S. Pat. No. 3,304,310; and suitable techniques for culturing *Rhodosporidium toruloides* are described in British Patent 2,060,610.

In the process of the invention, conditions can vary considerably. For example, the process can be carried out at a temperature of about −20° C. to about 30° C., at a pH of about 5 to about 9, for a time sufficient for completion of the reaction, typically about 5 minutes to 100 hours. Preferably the process is carried out at a temperature of about 0° C. to about 25° C., at a pH of about 7 to about 8, for about 10 minutes to about 48 hours (more preferably for about 30 minutes to 4 hours).

The process of the invention results in at least 4% or greater conversion of the compound of Formula II to the compound of Formula I, preferably at least 10% conversion, more preferably at least 50% conversion, and most preferably at least 80% conversion.

The process of the invention preferably includes the additional step of separating the desired product from the reaction medium. Such separation or isolation techniques are well known in the art. Such separation techniques include chromatography, extraction into an organic solvent, precipitation as insoluble material and recrystallization. A preferred separation technique is chromatography, particularly column chromatography. For example, the reaction medium can be vacuum treated to remove traces of unreacted acyl donor and impurities. The crude mixture can then be loaded on a preparative chromatography column (e.g., HP20SS). After washing with water, the desired product can be eluted with an appropriate solvent such as methanol. The desired product can then be obtained by standard crystallization techniques.

The following examples are to illustrate the invention but should not be interpreted as a limitation thereon.

EXAMPLE 1

Figure 1:
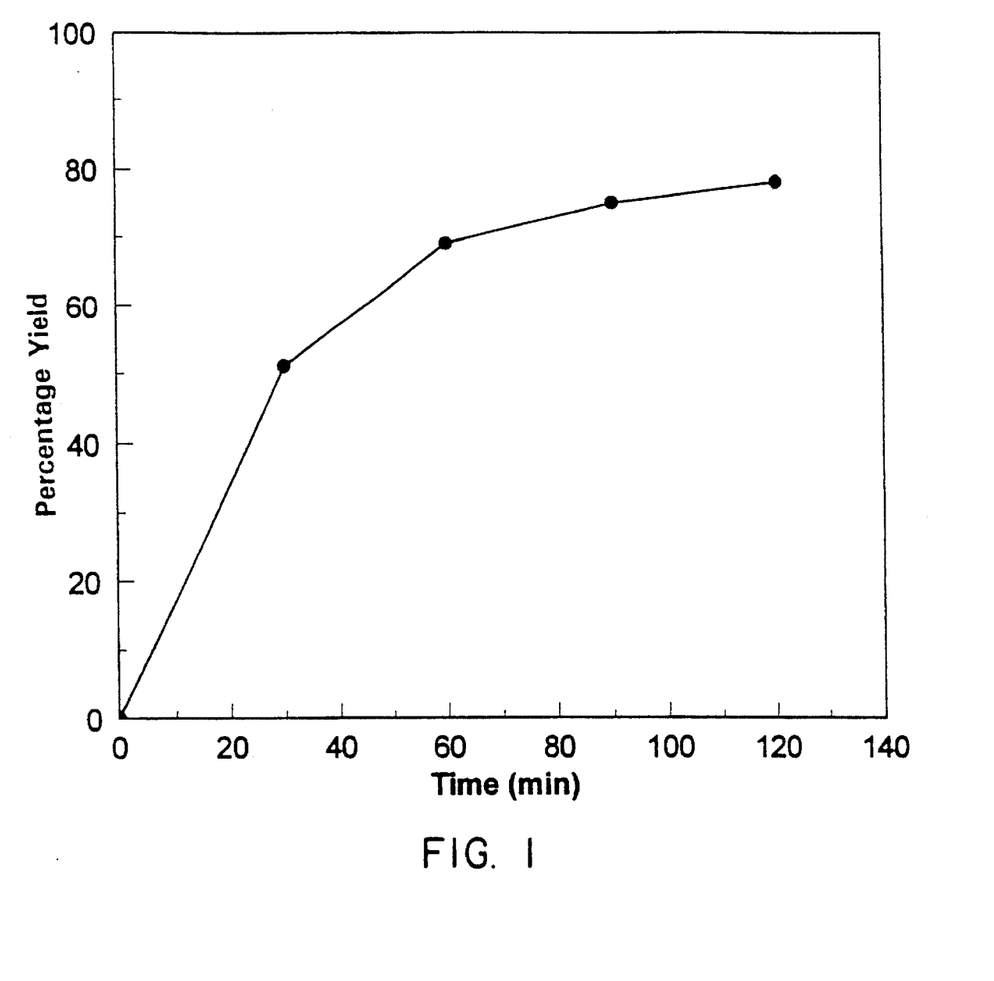
FIG. 1 - Percent conversion of des-7-ACA to 7-ACA vs. time for Example 1.

Synthesis of 7-ACA From des-7-ACA Using *R. toruloides* Whole Cells as the Enzyme Source and Isopropenyl Acetate as the Acyl Donor Shake flask fermentations of *Rhodosporidium toruloides* (ATCC 10657) for production of esterase were prepared according to the following protocol: Seed culture was initiated from the inoculation of frozen preservation cultures at 2% into a 500 mL flask containing 100 mL of the following medium: 2% glucose, 1% yeast extract, 1% Bactopeptone, 0.5% $KH_2PO_4$, pH 6.0. The medium was steam sterilized for 30 minutes. Seed flasks were cultured for 24 hours at 28° C. and 250 rpm, 2% inoculum volume was used to start production stage fermentations. Production stage medium was composed of: 8% corn steep liquor, 1% $K_2HPO_4$, 3% glucose, pH 6.2. The medium was steam sterilized in a 1L fermentor for 2 hours. Fermentor broth was cultured for 3 or 4 days at 16°–21° C. with high aeration. The activity of the esterase was monitored as follows: To 200 μL whole cells (diluted in distilled water to give substrate conversions of 10–20%) was added 200 μL potassium cephalosporin C at 20 mg/mL in 0.2M potassium phosphate buffer, pH 6.5. The mixture was incubated at 37° C. for 20 minutes and stopped by addition of 3.0 mL acetonitrile/water (1/1). The supernatant of the acetonitrile/water mixture was assayed by HPLC on a $C_{18}$ reverse phase column with the mobile phase consisting of 10 mM octanesulfonic acid, 0.1% $H_3PO_4$, 10% methanol, pH 2.5. Specific activities of whole broth were typically in the range of 20–37 International Units/mL (an International Unit, IU, is defined as one micromole of product formed per minute). *R. toruloides* washed-cell concentrate was prepared by centrifugation of whole cell broth and resuspension of cells to 80 units of activity per mL of water. Corn steep solids were removed by differential centrifugation. Desacetyl 7-ACA stock solution was prepared by addition of the solid at 333 mg/mL to 2M HEPES buffer pH 6.5–8.1, and adjustment of the pH to 7.8–8.0 with concentrated ammonia until dissolved. The volume of the solution was adjusted so that the final concentration of the substrate was 250 mg/mL des-7-ACA in 0.75 M HEPES buffer. Substrate stock solution (12.5 mL) and enzyme (12.5 mL) (*R. toruloides* cell concentrate at 80 IU/mL) were combined and the reaction initiated by addition of isopropenyl acetate (10 mL). The temperature was maintained at 20–24° C. and the pH was maintained at 6.5 by titration with concentrated ammonia. The reaction was constantly stirred and allowed to proceed for two hours or until product formation plateaued. The reaction was monitored by HPLC as previously described. FIG. 1 represents a typical reaction profile.

EXAMPLE 2

Synthesis of 7-ACA From des-7-ACA Using *R. toruloides* Whole Cells as the Enzyme Source and Triacetin as the Acyl Donor

Figure 2:
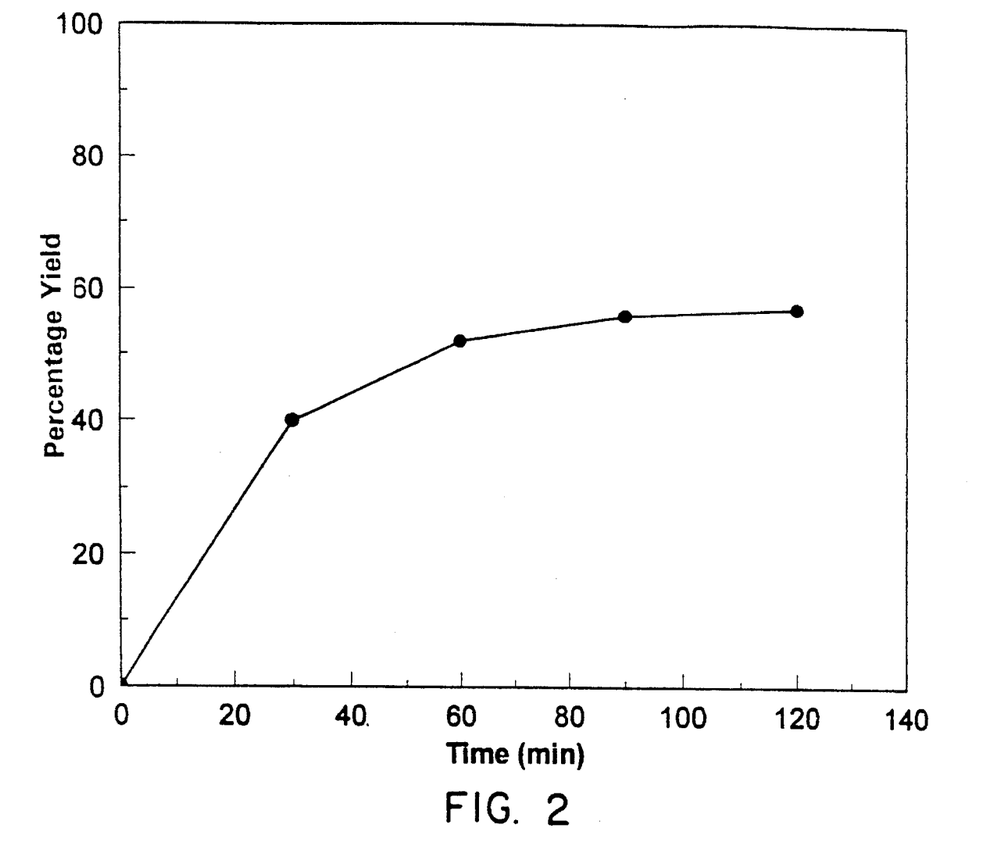
FIG. 2 - Percent conversion of des-7-ACA to 7-ACA vs. time for Example 2.

*R. toruloides* and des 7-ACA were prepared as described in Example 1. Incubation at 24° C. was initiated as described in Example 1 except that triacetin (10 mL) was added as the acetyl donor. A typical reaction profile with triacetin as the acyl donor is illustrated in FIG. 2.

EXAMPLE 3

Synthesis of 7-ACA From des-7-ACA Using *R. toruloides* Whole Cells as the Enzyme Source and Vinyl Acetate as the Acyl Donor 500 μL des 7-ACA stock solution (250 mg/mL in 750 mM HEPES buffer pH 7.8) was added to 500 μL cell stock. Sodium bisulfite (100 mg) was added to the mixture as an acetaldehyde scavenger. 260 μL vinyl acetate was added and the mixture was shaken and allowed to react at -20° C. The pH was maintained at 7.0 by addition of concentrated ammonia. The sample was removed from the −20°C. environment for periodic sampling during which time the temperature became elevated to between 0 and −10° C. Analysis of the mixture demonstrated approximately 73% conversion of des 7ACA to 7-ACA.

EXAMPLE 4

Synthesis of 7-ACA From des-7-ACA Using *R. toruloides* Whole Cells as the Enzyme Source and Various Acyl Donors

*R. toruloides* and des-7ACA were prepared as described in Example 1. Incubation at 24° C. was initiated as described in Example 1 or alternatively the reaction was scaled down to a 1.0 mL scale with the proportions remaining the same. The results of product formation using the various acyl donors are summarized in the following table.

TABLE 1

| Donor | Conversion (%) | Reaction Time (min) |
| --- | --- | --- |
| isopropenyl acetate | 82 | 150 |
| triacetin | 64 | 120 |
| vinyl acetate | 23 | 120 |
| ethyl acetate | 14 | 20 |
| diacetin | 22 | 120 |
| ethylene glycol diacetate | 49 | 120 |
| cis-1,4-diacetoxy butane | 29 | 60 |
| 1,4 diacetoxy butane | 23 | 35 |
| phenyl acetate | 49 | 35 |
| 1,2,4 triacetoxy benzene | 13 | 60 |
| 1,3-butanediol diacetate | 24 | 30 |
| 1,2 propanediol diacetate | 40 | 90 |
| n-butyl acetate | 4 | 30 |
| triethylene glycol diacetate | 32 | 150 |
| isopropyl acetate | 10 | 15 |
| isobutyl acetate | 9 | 30 |
| oxime ester (comparative) | 1.3 | 30 |

EXAMPLE 5

Synthesis of 7-ACA From des-7-ACA and Isopropenyl Acetate Using Esterase Released from *R. toruloides* Whole Cells by Treatment With EDTA at pH 4.0

*R. toruloides* was cultured as previously described in Example 1. The culture was treated with EDTA (0.1M) at pH 4.0 to release the esterase enzyme from the whole cells. The soluble enzyme was concentrated on a 30,000 molecular weight cut-off membrane yielding a final specific activity of 80 IU/mL. The synthesis of 7-ACA was carried out as described in Example 1 with the following exception: the reaction was carried out at 6° C. After 200 minutes the conversion yield to 7-ACA was 79%.

EXAMPLE 6

Synthesis of 7-ACA From des-7-ACA and Isopropenyl Acetate Using Immobilized Esterase From *R. toruloides*

*R. toruloides* was cultured as previously described in Example 1. Soluble esterase was obtained as described in Example 5. Soluble enzyme was treated with PEI (0.1%), and glutaraldehyde (0.5%). The mixture was stirred for 1 hour after which time the immobilized enzyme was recovered by filtration. The enzyme was washed with water and filtered again to give immobilized esterase enzyme of activity 350 IU/g. Synthesis of 7-ACA from des 7-ACA was carried out as in Example 1 with the following exceptions: the reaction was performed at 5° C. and 60 IU/mL of immobilized enzyme was used in the reaction mixture. After 180 minutes the conversion yield to 7-ACA was 76%.

EXAMPLE 7

Synthesis of 7-ACA From des-7-ACA Using *Bacillus subtilis* (ATCC 6633) Cell-Free Extract as the Enzyme Source and Various Acyl Donors Shake flask fermentations were prepared according to the following protocol. Seed stage was initiated from the inoculation of culture from a trypticase soy agar slant into a 125 mL flask with 25 mL trypticase soy media, and shaken at 250 rpm and 28° C. for 24 hours. Seed stage was inoculated at 1% into 20 production storage flasks containing 100 mL trypticase soy medium per 500 mL flask. The cultures were shaken at 250 rpm and 28° C. for 48 hours. 1800 mL of production stage whole broth was centrifuged, the cells were washed with 20 mM phosphate buffer pH 6.5, resuspended in a total of 90 mL and frozen. Thawed cells were further concentrated to 15 mL by centrifugation and resuspended to achieve a final esterase activity of 0.63 IU/mL.

Final cell concentrate (0.63 IU/mL) 500 µl was added to 500 µl des 7-ACA stock solution (Example 1). 400 µl of acetyl donor was added to initiate the reaction. The pH was initially maintained at 6.5–7.0 but was later increased to 8.0 to increase the rate of reaction. The pH was maintained at 8.0 for a total of 48 hours. Conversion yields to 7-ACA for the various acetyl donors are compared in the following table.

TABLE 2

| Donor | Conversion (%) |
| --- | --- |
| isopropenyl acetate | 16 |
| triacetin | 16 |
| triethylene glycol diacetate | 27 |
| ethylene glycol diacetate | 26 |

EXAMPLE 8

Synthesis of 7-ACA From des-7-ACA Using Concentrated *Bacillus subtilis* (ATCC 9466) Cell-Free Extract as the Enzyme Source and Ethylene Glycol Diacetate as the Acyl Donor Shake flask fermentations of *B. subtilis* for production of cephalosporin C esterase activity were performed as in Example 7. The extracellular enzyme from 1500 mL cell-free extract was concentrated by ultrafiltration over a 30,000 molecular weight cut-off membrane to a volume of 20 mL with specific activity of 40 IU/mL. 40 units of the enzyme were added to 1.0 mL stock des 7-ACA solution and 400 µL ethylene glycol diacetate were added to initiate the reaction. The pH of the reaction was maintained at 7.5 by addition of 2M NH$_3$. Another 400 µL aliquot of ethylene glycol diacetate was added at 60 minutes. At t=60, 120, and 180 minutes samples were taken and assayed for 7-ACA production as in Example 1. After 120 minutes 54% of the substrate had been converted to product. This level remained constant over the next 60 minutes.

EXAMPLE 9

Synthesis of 7-ACA From des-7-ACA Using Various Commercially Available Esterases and Lipases With Isopropenyl Acetate as the Acyl Donor Various commercially available lipases and esterases were screened for the ability to produce 7-ACA from des 7-ACA in the presence of isopropenyl acetate as the acyl donor. 500 μL des-7-ACA at 125 mg/mL (prepared similar to Example 1) was incubated with the various enzymes which had been suspended in 500 μL 20 mM phosphate buffer pH 6.5. 500 μL isopropenyl acetate was added to initiate the reaction and the pH was maintained at 7.0 with concentrated ammonia for 3 hours at 20°–24° C. The following enzymes were able to synthesize 7-ACA from des 7-ACA.

TABLE 3

| Enzyme | Amount | Conversion (%) |
| --- | --- | --- |
| Lipase type I from wheat germ (Sigma Chemical Co.) | 50 mg | 24 |
| Lipase from *Aspergillus niger* (Biocatalysts) | 100 mg | 13 |
| Acetylesterase from orange peel (Sigma Chemical Co.) | 250 μL | 14 |

EXAMPLE 10

Synthesis of Cephalosporin C From Desacetylcephalosporin C Using 7-ACA as the Acetyl Donor and Lipase,-Type I From Wheat Germ as the Enzyme Source Wheat germ lipase type I was incubated with desacetylcephalosporin C (200 mg/mL in Bis-Tris/MES buffer 300 mM/150 mM), 50 mg 7-ACA was added to initiate the reaction and the reaction was allowed to proceed at 20°–24° C., pH 7.0. The conversion yield to cephalosporin C was 19%.

EXAMPLE 11

Synthesis of 7-ACA From des-7-ACA Using Isopropenyl Acetate or Vinyl Acetate as the Acetyl Donor and Immobilized Lipase, Type I From Wheat Germ as the Enzyme Source Wheat germ (200 g) was mixed with water (800 mL) and ice (400 g), then homogenized in a blender for 1 minute and then again for 1 minute. The resulting mixture was treated with 0.1% PEI and stirred for 10 minutes at room temperature. The solution was centrifuged at 8000 rpm for 10 minutes to give clarified lipase extract. The extract was ultrafiltered through a 30,000 MWCO membrane and concentrated to 100 mL. The retentate was cooled to 4° C. and solid ammonium sulfate (40 g) was added over 10 minutes. The resulting mixture was centrifuged at 8000 rpm for 10 minutes. The protein pellet was dissolved by stirring in 30 mL water for 10 minutes at 4° C. The suspension was centrifuged at 8000 rpm for 10 minutes to give 50 mL of lipase concentrate. The concentrate was stirred at 4° C., celite (0.5 g) added, then 0.5 mL of 50% glutaraldehyde added over a period of 1 minute. The mixture was stirred for 4 minutes more, then one volume of cold acetone was added over a period of 2 minutes. The mixture was stored at 4° C. for 10 minutes. The immobilized enzyme was removed by filtration and resuspended in water. The pH was adjusted to 7.0, then enzyme refiltered to give 13.5 g of immobilized enzyme.

150 mg/mL of immobilized wheat germ lipase was combined with 150 mg/mL des 7-ACA and incubated in 1 mL 1M HEPES buffer, pH 7.8 at 25° C., 250 rpm for 4 hours. Vinyl acetate (0.1 mL) or isopropenyl acetate (0.10 mL) were added at t=0 and 150 minutes. After four hours conversion yields of 7-ACA were 18% and 7% for vinyl acetate and isopropenyl acetate respectively.

EXAMPLE 12

Acetylation of Phenylacetyl Desacetyl 7-ACA

A mixture was made of the following components: phenylacetyl-desacetyl 7-ACA (50 mg), 2M MES/NH$_4^+$ buffer (0.5 mL), methyl acetate (4.5 mL), isopropenyl acetate (0.5 mL) and a suspension of *Rhodosporidium toruloides* cells (150 IU/mL; 0.5 mL). The mixture was stirred for 2 hours at 25° C. (allowing the pH to fall to -6.0). At this time the reaction mixture showed by TLC an approximately 50:50 mixture of unreacted phenylacetyl-desacetyl 7-ACA and phenylacetyl 7-ACA (by comparison with authentic compounds).

EXAMPLE 13

Figure 3:
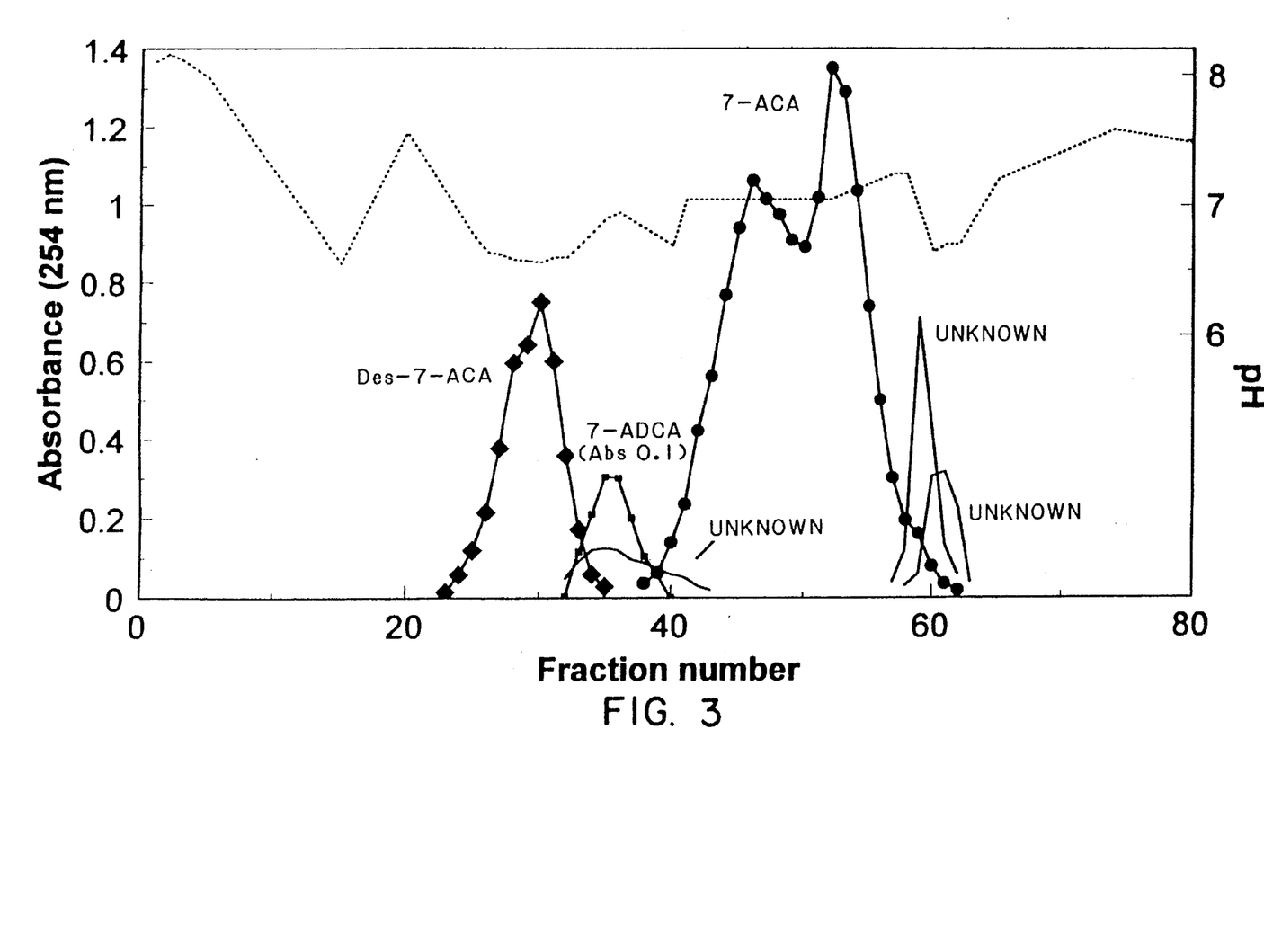
FIG. 3 - Absorbance at 254 nanometers (nm) vs. fraction number for the separation described in Example 13.

Separation of Synthetic 7-ACA From 7-ADCA and Unreacted Desacetyl 7-ACA 50 mL of a reaction mixture as described in Example 1 was vacuum treated to remove traces of acetone and unreacted isopropenyl acetate. The final concentration of 7-ACA was 2.45% and desacetyl 7-ACA 1.25%. The sample was loaded onto a preparative p20ss column (4×30 cm). The column was washed with 150 mL distilled water and the product was eluted with 10% methanol, 10 mL fractions were collected. A typical column profile is shown in FIG. 3. The 7-ACA peak fractions were pooled (100mL) and concentrated into a final volume of 20 mL by rotary evaporation. The pH was lowered to 4.2 with 6N HCL, 10 mL of methanol was added and the sample chilled. The resulting solid was collected by filtration. Recovery of 7-ACA was 65%, with 5% desacetyl 7-ACA remaining and <0.1% of 7-ADCA present.

We claim:

1. An acylation process for the preparation of a cephalosporin compound of the formula wherein

R' is hydrogen or an acyl group of the formula wherein R is the residue of a carboxylic acid, X is hydrogen or halo, and G is sulphur, oxygen, sulphoxide, sulphone, or methylene; which comprises reacting in an aqueous medium a compound of the formula with an acyl donor containing at least three carbon atoms and an enzyme selected from the group consisting of *Rodosporidium toruloides* esterase, wheat germ lipase, *Aspergillus niger* lipase, orange peel acetylesterase and *Bacillus subtilis* esterase whereby said cephalosporin compound is produced.

2. The process of claim 1 when said enzyme is *Rhodosporidium toruloides* esterase.

3. The process of claim 1 when said enzyme is obtained from *Rhodosporidium toruloides* ATCC 10657.

4. The process of claim 1 wherein R' is hydrogen, acetyl, glutaryl, α-aminoadipyl, or phenylacetyl, G is sulphur, and X is hydrogen.

5. The process of claim 4 when G is sulphur.

6. The process of claim 4 wherein R' is hydrogen.

7. The process of claim 5 wherein R' is hydrogen.

8. The process of claim 1 wherein said acyl donor is of the formula wherein R" is $C_1$–$C_{10}$ alkyl, $C_2$–$C_{10}$ alkenyl, $C_3$–$C_{10}$ cycloalkyl, $C_3$–$C_{10}$ cycloalkenyl, $C_2$–$C_{10}$ alkynyl, $C_6$–$C_{30}$ aryl, $C_1$–$C_{10}$ substituted alkyl, $C_2$–$C_{10}$ substituted alkenyl, $C_3$–$C_{10}$ substituted cycloalkyl, $C_3$–$C_{10}$ substituted cycloalkenyl, $C_6$–$C_{30}$ substituted aryl, a group of the formula wherein n is an integer of 2 or greater and R''' is H or acetyl or group of the formula wherein n and R''' are as defined above; and X is hydrogen or halo.

9. The process of claim 8 wherein R" is $C_2$–$C_6$ alkenyl, $C_1$–$C_6$ alkyl substituted with 1–3 acetoxy groups, $C_6$–$C_{10}$ aryl, or a group of the formula wherein n is an integer of 2 to 100.

10. The process of claim 1 wherein the acyl donor is isopropenyl acetate, triacetin, vinyl acetate, ethyl acetate, diacetin, ethylene glycol diacetate, cis-1,4-diacetoxy butane, 1,4-diacetoxy butane, phenyl acetate, 1,2,4-triacetoxy benzene, 1,3-butanediol diacetate, 1,2-propanediol diacetate, n-butyl acetate, triethylene glycol diacetate, isopropyl acetate, or isobutyl acetate.

11. The process of claim 4 wherein the acyl donor is isopropenyl acetate, triacetin, vinyl acetate, ethyl acetate, diacetin, ethylene glycol diacetate, cis-1,4-diacetoxy butane, 1,4-diacetoxy butane, phenyl acetate, 1,2,4-triacetoxy benzene, 1,3-butanediol diacetate, 1,2-propanediol diacetate, n-butyl acetate, triethylene glycol diacetate, isopropyl acetate, or isobutyl acetate.

12. The process of claim 7 wherein the acyl donor is isopropenyl acetate, triacetin, vinyl acetate, ethyl acetate, diacetin, ethylene glycol diacetate, cis-1,4-diacetoxy butane, 1,4-diacetoxy butane, phenyl acetate, 1,2,4-triacetoxy benzene, 1,3-butanediol diacetate, 1,2-propanediol diacetate, n-butyl acetate, triethylene glycol diacetate, isopropyl acetate, or isobutyl acetate.

13. The process of claim 1 wherein the acyl donor is isopropenyl acetate, triacetin, vinyl acetate, diacetin, ethylene glycol diacetate, cis-1,4-diacetoxy butane, 1,4-diacetoxy butane, phenyl acetate, 1,3-butanediol diacetate, 1,2-propanediol diacetate, or triethylene glycol diacetate.

14. The process of claim 4 wherein the acyl donor is isopropenyl acetate, triacetin, vinyl acetate, diacetin, ethylene glycol diacetate, cis-1,4-diacetoxy butane, 1,4-diacetoxy butane, phenyl acetate, 1,3-butanediol diacetate, 1,2-propanediol diacetate, or triethylene glycol diacetate.

15. The process of claim 7 wherein the acyl donor is isopropenyl acetate, triacetin, vinyl acetate, diacetin, ethylene glycol diacetate, cis-1,4-diacetoxy butane, 1,4-diacetoxy butane, phenyl acetate, 1,3-butanediol diacetate, 1,2-propanediol diacetate, or triethylene glycol diacetate.

16. The process of claim 1 carried out at a temperature of about −20° C. to about 30° C., at a pH of about 5 to about 9, for about 5 minutes to 100 hours.

17. The process of claim 1 carried out at a temperature of about 0° C. to about 25° C., at a pH of about 7 to about 8, for about 30 minutes to 4 hours.

18. The process of claim 1 including the additional step of separating the cephalosporin compound which is produced from the reaction medium.

19. The process of claim 16 wherein the separation is performed by chromatography.

20. The process of claim 3 wherein the enzyme source is whole is soluble enzyme obtained after EDTA treatment of cells, or immobilized enzyme obtained by glutaraldehyde/PEI treatment of soluble enzyme.

* * * * *